(12) United States Patent
Liu et al.

(10) Patent No.: US 8,002,776 B2
(45) Date of Patent: Aug. 23, 2011

(54) VERTEBRAL ENDPLATE PREPARATION TOOL KIT

(75) Inventors: Mingyan Liu, Bourg la Reine (FR); Loic Josse, Denens (CH)

(73) Assignee: Warsaw Orthopedic, Inc., Warsaw, IN (US)

( * ) Notice: Subject to any disclaimer, the term of this patent is extended or adjusted under 35 U.S.C. 154(b) by 1284 days.

(21) Appl. No.: 11/224,647

(22) Filed: Sep. 12, 2005

(65) Prior Publication Data

US 2006/0129160 A1    Jun. 15, 2006

Related U.S. Application Data

(63) Continuation of application No. PCT/IB03/00910, filed on Mar. 13, 2003.

(51) Int. Cl.
*A61B 17/00* (2006.01)
(52) U.S. Cl. .......................................................... 606/85
(58) Field of Classification Search .................... 606/80, 606/85; 451/162, 163, 164, 356; 74/42
See application file for complete search history.

(56) References Cited

U.S. PATENT DOCUMENTS

| | | | | |
|---|---|---|---|---|
| 1,700,114 A | * | 1/1929 | Thompson | 451/356 |
| 1,789,804 A | * | 1/1931 | Broillet | 30/369 |
| 2,584,590 A | * | 2/1952 | Julian | 30/43.8 |
| 2,590,452 A | * | 3/1952 | Peterson | 30/34.2 |
| 3,897,630 A | * | 8/1975 | Glover et al. | 30/220 |
| 3,914,906 A | * | 10/1975 | Barnes | 451/356 |
| 4,466,429 A | * | 8/1984 | Loscher et al. | 606/180 |
| 4,920,652 A | * | 5/1990 | Johnson | 30/504 |
| 5,581,891 A | * | 12/1996 | Wheeler et al. | 30/216 |
| 5,725,530 A | * | 3/1998 | Popken | 606/82 |
| 5,759,093 A | * | 6/1998 | Rodriguez | 451/356 |
| 6,692,501 B2 | * | 2/2004 | Michelson | 606/80 |
| 2001/0039427 A1 | | 11/2001 | Dinger et al. | |
| 2002/0058944 A1 | | 5/2002 | Michelson | |
| 2002/0165550 A1 | | 11/2002 | Frey et al. | |
| 2006/0200153 A1 | * | 9/2006 | Harp | 606/85 |

\* cited by examiner

*Primary Examiner* — Thomas C Barrett
*Assistant Examiner* — David W Bates

(57) ABSTRACT

A disc preparation system includes an oscillating rasp for preparation of vertebral endplates and a central reamer for reaming a pair of kidney-shaped grooves into the vertebral endplate. The oscillating rasp is powered by a rotary power source. A linkage assembly is coupled to the rotary power source to convert the rotary motion into a reciprocating motion. A pair of rasps plates, which are linked to the linkage assembly, linearly reciprocate in opposite directions in response to the reciprocating motion of the linkage assembly. In one form, the central reamer includes a pair of cutting elements that are coupled to the rotary power source in order to rotate in response to rotational movement from the rotary power source. In another form, the central reamer includes a single cutting element coupled to an angled reamer handle and a reamer guide.

17 Claims, 6 Drawing Sheets

US 8,002,776 B2

VERTEBRAL ENDPLATE PREPARATION TOOL KIT

CROSS REFERENCE TO RELATED APPLICATIONS

The present application is a continuation of International PCT Application No. PCT/IB2003/000910, filed on Mar. 13, 2003 and published on Sep. 23, 2004 as International Publication No. WO 2004/080316, the entire contents of which are hereby incorporated by reference.

FIELD OF THE INVENTION

The present invention generally relates to vertebral endplate tools, and more specifically, but not exclusively, concerns vertebral endplate tools that are used to form a centrally located cavity in vertebral endplates.

BACKGROUND

Intervertebral discs, located between the endplates of adjacent vertebrae, stabilize the spine, distribute forces between the vertebrae and cushion the vertebral bodies. An intervertebral disc may deteriorate due to trauma, aging, or disease resulting in pain or discomfort to a patient. One common procedure for relief of patient discomfort is a disectomy, or surgical removal of all or part of the intervertebral disc. Often, this is followed by implantation of a device or spinal implant between the adjacent vertebrae in order to maintain or restore disc space height. Through stabilization of the vertebrae, the risk of reoccurrence of the same disabling back pain due to persistent inflammation and/or instability is reduced.

During implantation of a spinal implant, the endplates of adjacent vertebrae are sometimes milled to ensure firm implantation of the spinal implant by promoting bone ingrowth. One problem faced with typical milling instrumentation is that it is unable to form precise cavities at desired locations in the endplates. If not precisely prepared, the formed disc space may result in the expulsion of the implant, which can lead to injury of the patient.

Moreover, precise control of the milling equipment is required in order to avoid damaging vital tissues along the spinal column, such as nerves. During milling, the surgeon has to apply force to the milling equipment in order to counteract the forces created by the milling equipment cutting into the vertebrae. If not counteracted, the resultant force can cause the milling equipment to cut into portions of the vertebrae not intended to be milled.

Thus, there remains a need for implant endplate preparation tools that are capable of precisely defining cavities for securing implants.

SUMMARY

The present invention contemplates intervertebral endplate tools that have a reduced profile and that can precisely prepare a cavity for insertion of a device for spacing adjacent vertebrae.

In one aspect, an oscillating rasp, which is used to prepare vertebral endplates, includes a rotary power source and a linkage assembly coupled to the rotary power source, which converts rotary motion of the rotary power source into a reciprocating motion. A pair of bilateral rasp plates is linked to the linkage assembly. The pair of bilateral rasp plates are adapted to linearly reciprocate in opposite directions in response to the reciprocating motion of the linkage assembly.

In another aspect, a central reamer is used to ream a pair of kidney-shaped grooves into a vertebral endplate. The reamer includes a rotary power source operable to rotate about a drive axis. A pair of cutting elements are coupled to the rotary power source. The cutting elements are adapted to rotate about a cutting axis in response to rotational movement of the rotary power source about the drive axis. The drive axis is arranged in a perpendicular arrangement with respect to the cutting axis.

In a further aspect, a kit includes an oscillating rasp to prepare surfaces of vertebral endplates. The kit further includes cutter configured to cut a guide slot into the vertebral endplates and a reamer. The reamer has a guide flange adapted to be slidably received in the guide slot, and the reamer has a cutting element adapted to cut a cavity into the vertebral endplates.

Another aspect concerns a method that includes rasping a generally flat surface on an endplate of a vertebrae with a rasp having a pair of bilateral rasp plates linearly reciprocating in opposite directions. A kidney-shaped central cavity is reamed within the flat surface with a cutting element of a central reamer.

DESCRIPTION OF THE PREFERRED EMBODIMENTS

Figure 1:
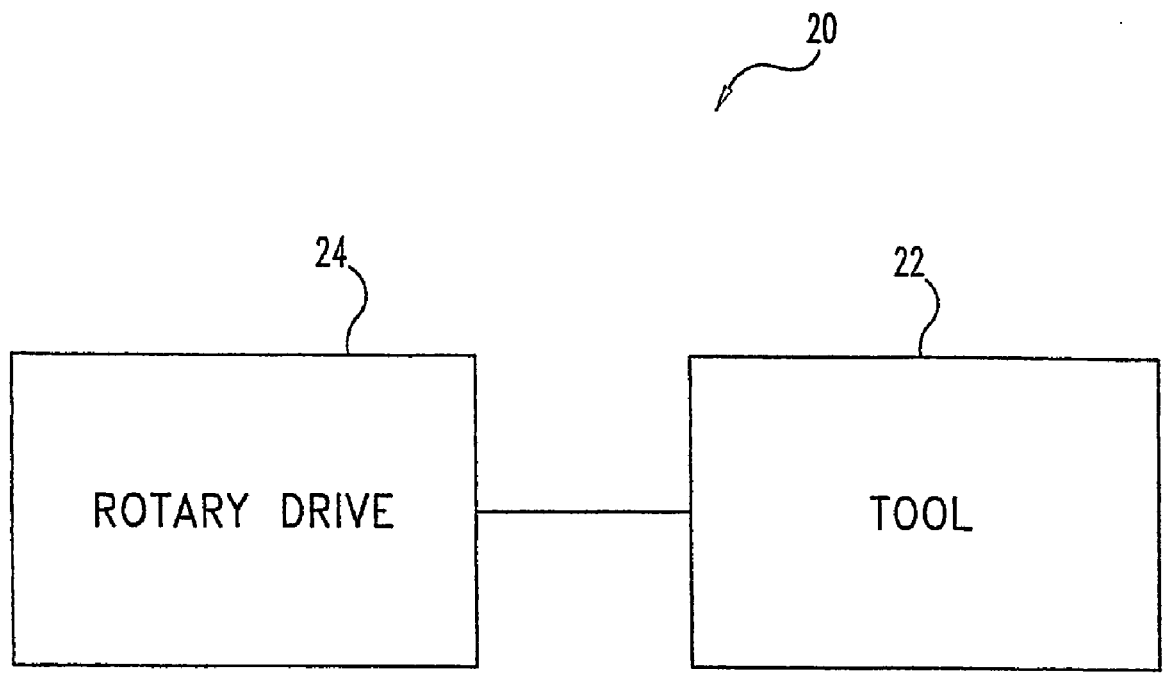
FIG. 1 shows a diagrammatic view of a tool assembly according to one embodiment.

For the purposes of promoting an understanding of the principles of the insertion, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail, although it will be apparent to those skilled in the art that some of the features which are not relevant to the invention may not be shown for the sake of clarity.

A tool system or assembly 20 according to one embodiment is illustrated in diagrammatic form in FIG. 1. As shown, tool assembly 20 includes a disc preparation tool 22 that is coupled to a rotary drive 24. As will be described in detail below, the tool 22 is used in preparing a disc space for insertion of an intervertebral spacer. The rotary drive 24 supplies power to the tool 22, and the disc preparation tool 22 converts the rotary motion of the rotary drive 24 into a cutting motion in order to prepare the disc space. By way of a non-limiting example, the rotary drive 24 can include a pneumatic motor, an electric motor, and/or a manually operated, rotary drive handle, to name a few. In one embodiment, the rotary drive 24 is a pneumatic motor that is operable to supply rotary movement to the tool 22.

Figure 2:
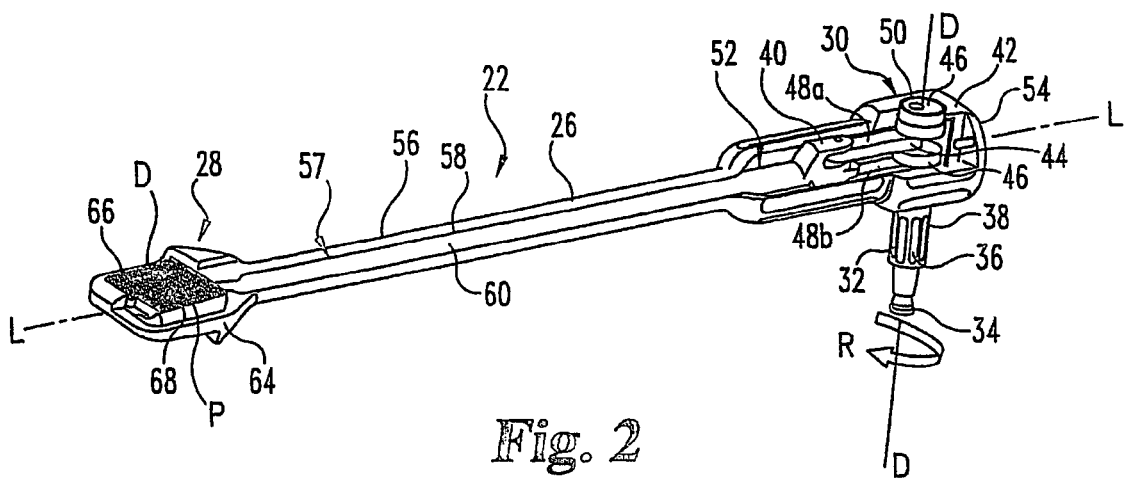
FIG. 2 is a partial cross-sectional, perspective view of a reciprocating rasp according to a further embodiment.

One version of tool 22 that can be used in system 20 is illustrated in FIG. 2. As illustrated, oscillating rasp 26 includes a distal end portion 28 and a proximal end portion 30. The proximal end portion 30 includes a drive shaft 32 that is adapted to connect to the rotary drive 24. As depicted in FIG. 2, the drive shaft 32 has an attachment head 34 and a drive portion 36 that has a plurality of drive ridges 38 radially oriented along the drive shaft 32. The drive ridges 38 are adapted to engage the rotary drive 24 such that the rotary drive 24 is able to rotate the drive shaft 32.

Within housing 40, the rasp 26 includes a linkage assembly 42 that converts the rotary motion R of the drive shaft 32 about drive axis D into a linear reciprocating motion along longitudinal skis L of the rasp 26. As illustrated in FIG. 2, the linkage assembly 42 includes a crankshaft 44 with a pair of cranks 46 pivotally coupled to a pair of connecting rods 48 (48a, 48b). The linkage assembly 42 is connected to the drive shaft 32. Opposite the drive shaft 32, along the drive axis D, the linkage assembly 42 includes a bearing 50 rotatably mounted within the housing 40, thereby allowing rotation of the crankshaft 44. As should be appreciated, the linkage assembly 42 can include a second bearing 50 that is located between the drive shaft 32 and the cranks 46. As shown, the connecting rods 48 are positioned one hundred and eighty-degrees (180°) out of phase with respect to one another on the crankshaft 44 such that when one connecting rod 48a is extended along the longitudinal axis L towards the distal end portion 28, the other connecting rod 48b is retracted away from the distal end portion 28. The linkage assembly 42 is received within a cavity 52 defined in the housing 40. An end cap 54 of the housing 40 seals the linkage assembly 42 within the cavity 52. A shaft portion 56 connects the distal end portion 28 of the rasp 26 to the proximal end portion 30. The shaft portion 56 defines in the housing 40 a longitudinal cavity 57, which communicates with cavity 52. As shown, a pair of rod members 58, 60 is received within the cavity 57 of the shaft portion 56 of the housing 40. Each of the rod members 58, 60 is pivotally connected to one of the connecting rods 48 near the proximal end 30.

Figure 3:
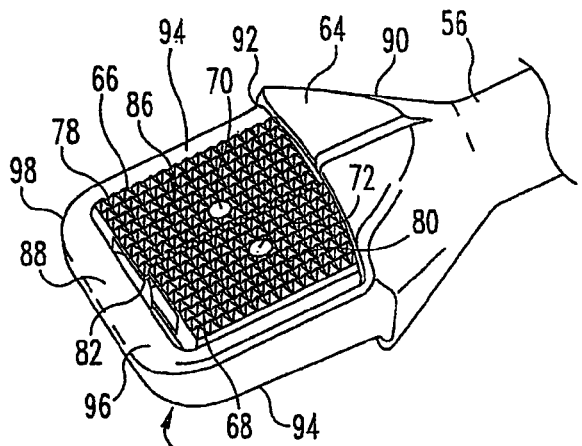
FIG. 3 is an enlarged perspective view of a head portion of the FIG. 2 rasp.
Figure 4:
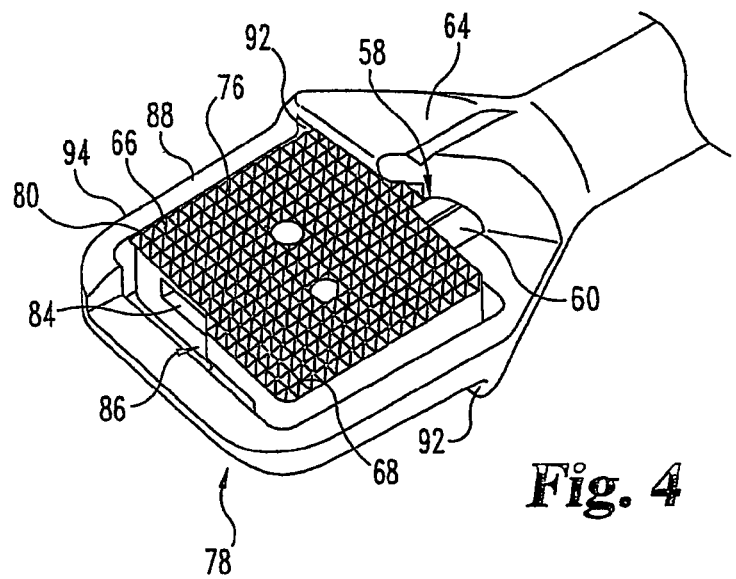
FIG. 4 is a partial cross sectional view of the head shown in FIG. 3.

At distal end portion 28, the rasp 26 includes a head portion 64 that has a pair of rasp plate or cutting members 66, 68 that are used to cut a rectangular cavity into an endplate of a vertebral body plate. As shown in greater detail in FIGS. 3 and 4, the first rasp plate 66 and the second rasp plate 68 are connected to the first rod member 58 and the second rod member 60, respectively. First 70 and second 72 pins respectively secure the rasp plates 66 and 68 to the rods 58 and 60. Upper 76 and lower 78 surfaces of the rasp plates 66, 68 are textured to have cutting members 80 that are configured to cut into a pair of opposing vertebral endplates. In the illustrated embodiment, the cutting members 80 have a pyramidal shape. As should be appreciated, the upper and lower surfaces 76, 78 can include other types of texturing in order to cut into the endplates.

To ensure that the first 66 and second 68 rasp plates do not separate from one another during use, the first rasp plate 66 has a tongue member 82 received within a groove 84 in the second rasp plate 68. As illustrated, the rasp plates 66, 68 each have a generally rectangular shape, and when placed side by side, have an overall rectangular shape. Both rasp plates 66 and 68 are received within a cavity 86 defined by a u-shaped end member 88 of the housing 40. At transition portion 90, the head portion 64 gradually tapers to the shaft portion 56. The transition portion 90 further includes a pair of opposing stop surfaces 92 that extend above and below the rasp plates 66, 68 in order to prevent the rasp 26 from penetrating too far into the vertebrae along the longitudinal axis L. Moreover, the u-shaped end member 88 has upper and lower surfaces 94 that limit the penetration depth of the rasp plates 66, 68 into the vertebrae. The u-shaped end member 88 includes a tapered insertion portion 96 that is tapered to make insertion of the rasp 26 between the vertebrae easier, and corners 98 of the u-shaped end member 88 are rounded to minimize tissue damage.

Referring again to FIG. 2, when the drive shaft 32 is rotated by the rotary drive 24, the linkage assembly 42 converts the rotary motion R into a reciprocating linear motion along the longitudinal axis L. In the rasp 26, the alternating reciprocating motion of the connecting rods 48a, 48b and the rod members 58, 60, which is created by the rotation of the crankshaft 44, alternatingly reciprocates the rasp plate 66 and 68 in opposite, distal D and proximal P directions along the longitudinal axis L. By having the rasp plates 66 and 68 oscillate in longitudinally opposite directions, the rectangular cavity formed by the rasp 26 can have a more precise shape because the forces imparted by the oppositely moving rasp plate 66, 68 counteract one another, thereby minimizing the resultant force imparted on the proximal end portion 30 of the rasp 26. During surgery, the surgeon has to apply little or no force to counteract the cutting forces generated by the rasp plates 66, 68. Thus, the oscillating rasp 26 according to this embodiment is able to convert rotary force into a linear force such that a precisely dimensioned finished surface can be formed.

Figure 5:
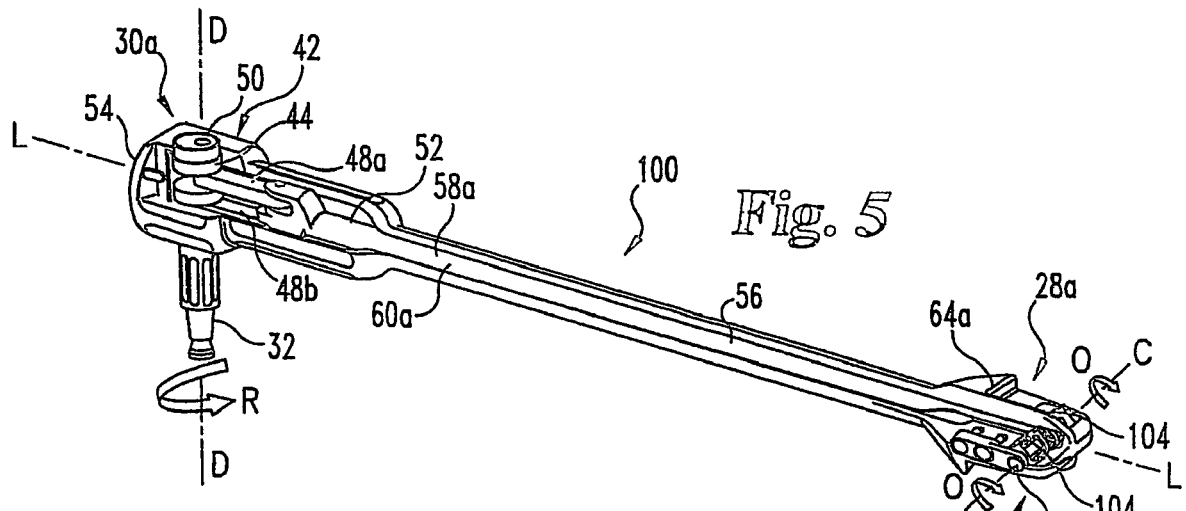
FIG. 5 is a cross sectional, perspective view of a central reamer according to another embodiment.
Figure 6:
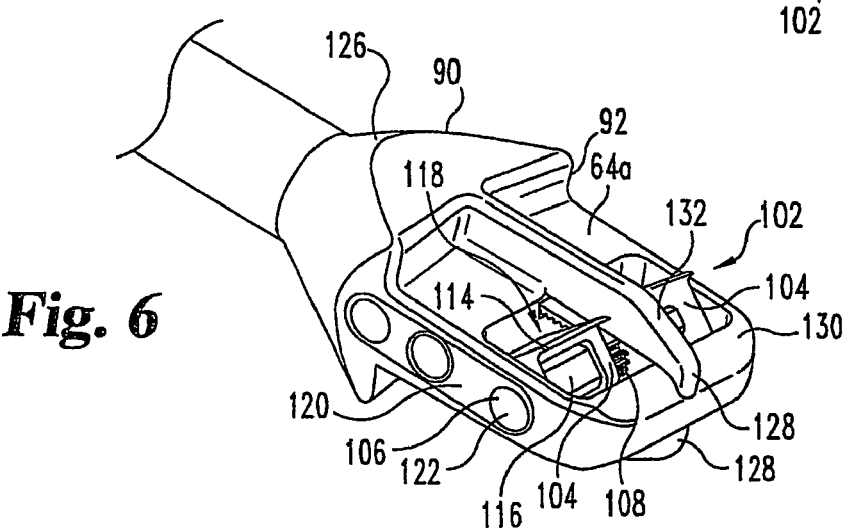
FIG. 6 is an enlarged perspective view of a head portion of the FIG. 5 reamer.
Figure 7:
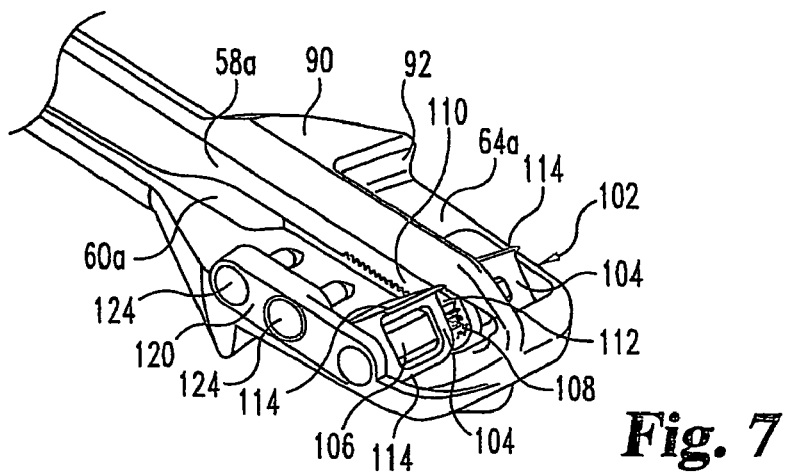
FIG. 7 is an enlarged cross sectional view of the head shown in FIG. 6.

Another version of tool 22 is a central reamer 100 that is illustrated in FIGS. 5-7. As shown, the central reamer 100 includes a distal end portion 28a and an opposite proximal end portion 30a. The reamer 100 includes a number of components similar to the ones described above for the rasp 26. Like rasp 26, the central reamer 100 includes a drive shaft 32 linkage assembly 42 with a crankshaft 44. The crankshaft 44 includes a pair of cranks 46 each connected to a respective connecting rod 48. The crankshaft 44 is supported in housing 56 by bearings 50. The housing 56 forms central cavity 52 that is enclosed by end cap 54. The shaft portion 56 of the reamer 100 slidingly receives first 58a and second 60a rod members. The rod members 58a and 60a are connected to connecting rods 48a and 48b, respectively. As shown, rod members 58a and 60a differ from the previous embodiment at head portion 64a of the reamer 100.

As is shown in FIGS. 6 and 7, the head portion 64a of the reamer 100 includes a cutting assembly 102, which is used to cut kidney-shaped cavities into a pair of adjacent endplates. As illustrated, the cutting assembly 102 includes a pair of bilaterally oriented cutting members 104 mounted on a rotatable cutting shaft 106. A pinion gear 108 is mounted on the cutting shaft 106 between the cutting members 104. Both rod members 58a and 60a have rack members 110 and 112, respectively, with teeth that engage the pinion gear 108. As shown, the rack members 110 and 112 are positioned at opposite sides of the pinion gear 108. As the drive shaft 32 is rotated, the linkage assembly 42, through camshaft 44 and connecting rods 48, convert the rotary motion R of shaft 32 into a reciprocating linear motion along the longitudinal axis L of the central reamer 100. The rod members 58a and 60a reciprocate in an alternating manner along the longitudinal axis of the reamer 100. With the rack members 110 and 112 moving in an alternating manner, the pinion gear 108 is rotated in an oscillating fashion such that the cutting members 104 are rotated in an oscillating direction, as indicated by arrows O in FIG. 5, about a cutting axis C and cutting shaft 106. As illustrated, the cutting axis C is oriented perpendicular to both the longitudinal axis L as well as the drive axis D.

With continued reference to FIGS. 6 and 7, the cutting members 104 have a generally rectangular cross-sectional or box shape. Openings 116 are formed in the cutting members 104 between the individual cutting blades 114 so as to allow bone chips to be removed during cutting. Cutting members 104 along with the cutting shaft 106 are received in a cutting shaft cavity 118 defined in the head portion 64a. A shaft support member 120 rotatably supports the cutting shaft 106, and one end of the cutting shaft 106 is received within a shaft opening 122 defined in support member 101. As shown, a pair of screws 124 secure the shaft support member 120 to the head portion 64a. The other end of the cutting shaft 106 is supported by a second shaft opening 122 formed in the head 64a. Referring to FIG. 7, the head portion 64a includes a pair of opposing vertebrae engaging surfaces 126 that are adapted to fit between and engage adjacent vertebrae. A pair of guide members 128, which guide and center the reamer 100 when inserted between the adjacent vertebrae, bisect the vertebrae engaging surfaces 126. At the end opposite of surface 122, the engaging surfaces 126 and the guide member 128 respectively have tapered portions 130 and 132, which aid in the insertion of the head portion 64a between the adjacent vertebrae.

Figure 8:
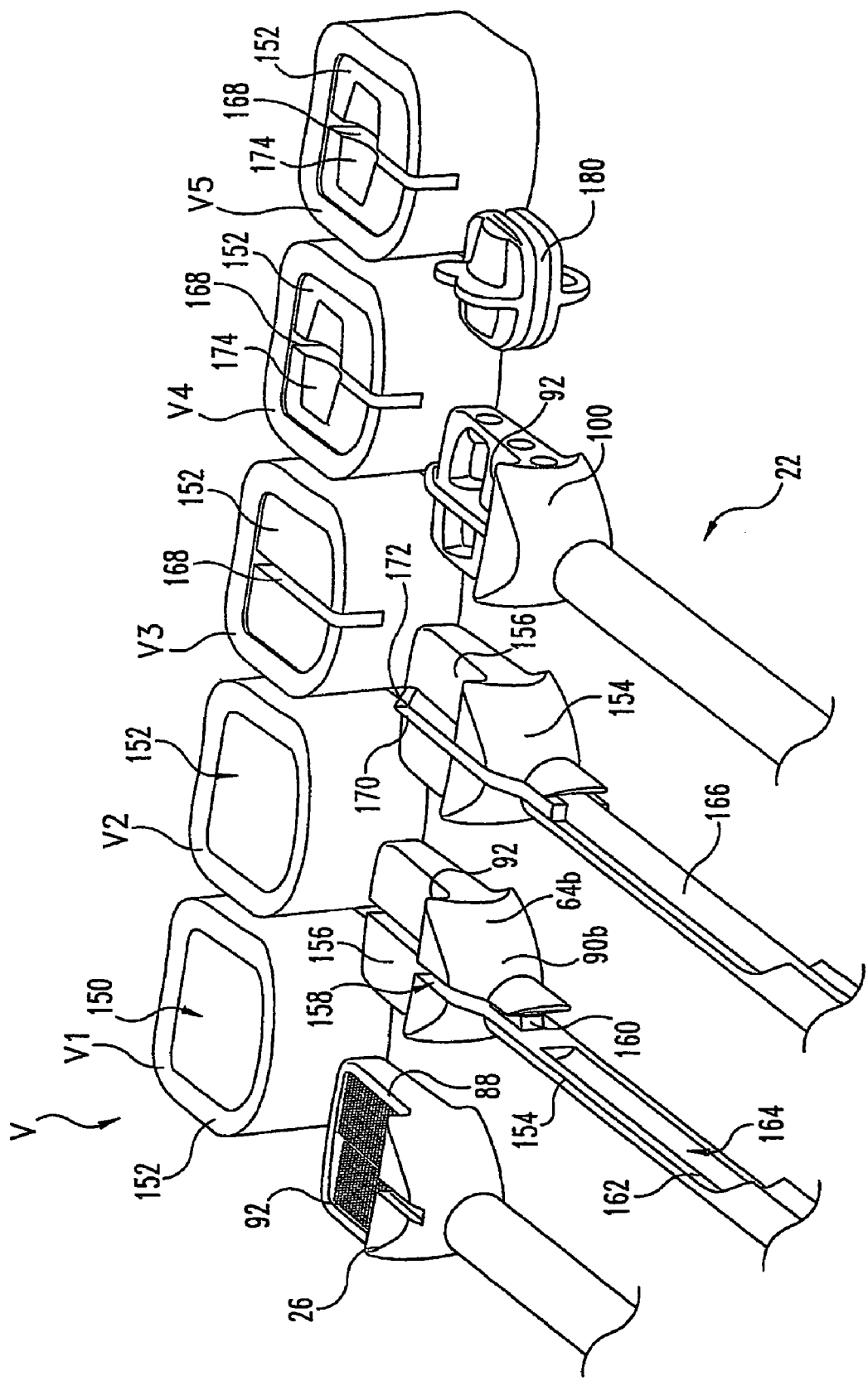
FIG. 8 illustrates the stages involved in preparation of a disc space for implantation of an implant according to one embodiment.

FIG. 8 illustrates how the tools 22 according to the present invention are used to progressively shape a vertebra V. The illustrated vertebra V has been numbered V1-V5 in order to show the progression of the cavities formed for insertion of a spacer into the vertebra V. However, it should be understood that the progressive numbering of vertebrae V1-V5 is for explanation purposes only in order to merely show the progression in which a single vertebra V is shaped during a shaping technique according to the present invention. Moreover, although only a single vertebra V is illustrated, it should be understood that the illustrated cavity forming technique can occur at the same time on both opposing vertebrae in a disc space. As depicted, the oscillating rasp 26 removes a cartilage layer and prepares a regular flat surface or cavity 150 in the endplate 152 without cutting into spongy bone of the vertebrae V. Cavity 150 in the illustrated embodiment has a substantially rectangular shape, but it should be appreciated that the shape of cavity 150 can be different in order to accommodate differently shaped implants. The u-shaped end member of the rasp 26 ensures that the rasp 26 does not cut too deeply into the endplate 152 of the vertebrae V1. Moreover, the stop surfaces 92 prevent the rasp 26 from being inserted at an excessive depth into the vertebra V1. Following cutting of the rectangular cavity 152, as shown with vertebra V2, a midline cutter support 154 is inserted into central cavity 152. As mentioned above, the rasp 26 removes the cartilage layers and prepares regular flat surface or cavities 150 without cutting into spongy bone in the vertebrae V. As depicted, the midline cutter support 154 has a pair of vertebrae engaging surfaces 156, each of which are bisected by a cutter slot 158. A connecting member 160 connects the two halves of the head portion 64b of the midline cutter support 154. The midline cutter support 154 further includes a handle portion 162 that defines a midline cutter cavity 164. As shown with vertebra V3, cutter 166 is received within the midline cutter cavity 164 and cutter slot 158 in order to cut a midline center slot 168. The cutter 166 has a blade portion 170 that extends above the vertebrae engaging surfaces 156 in order to cut the slot 168 in the vertebrae V3. As illustrated, the blade 170 has a tapered end 172 to coincide with tapered portion 132 on guide member 128 of the central reamer 100.

Figure 9:
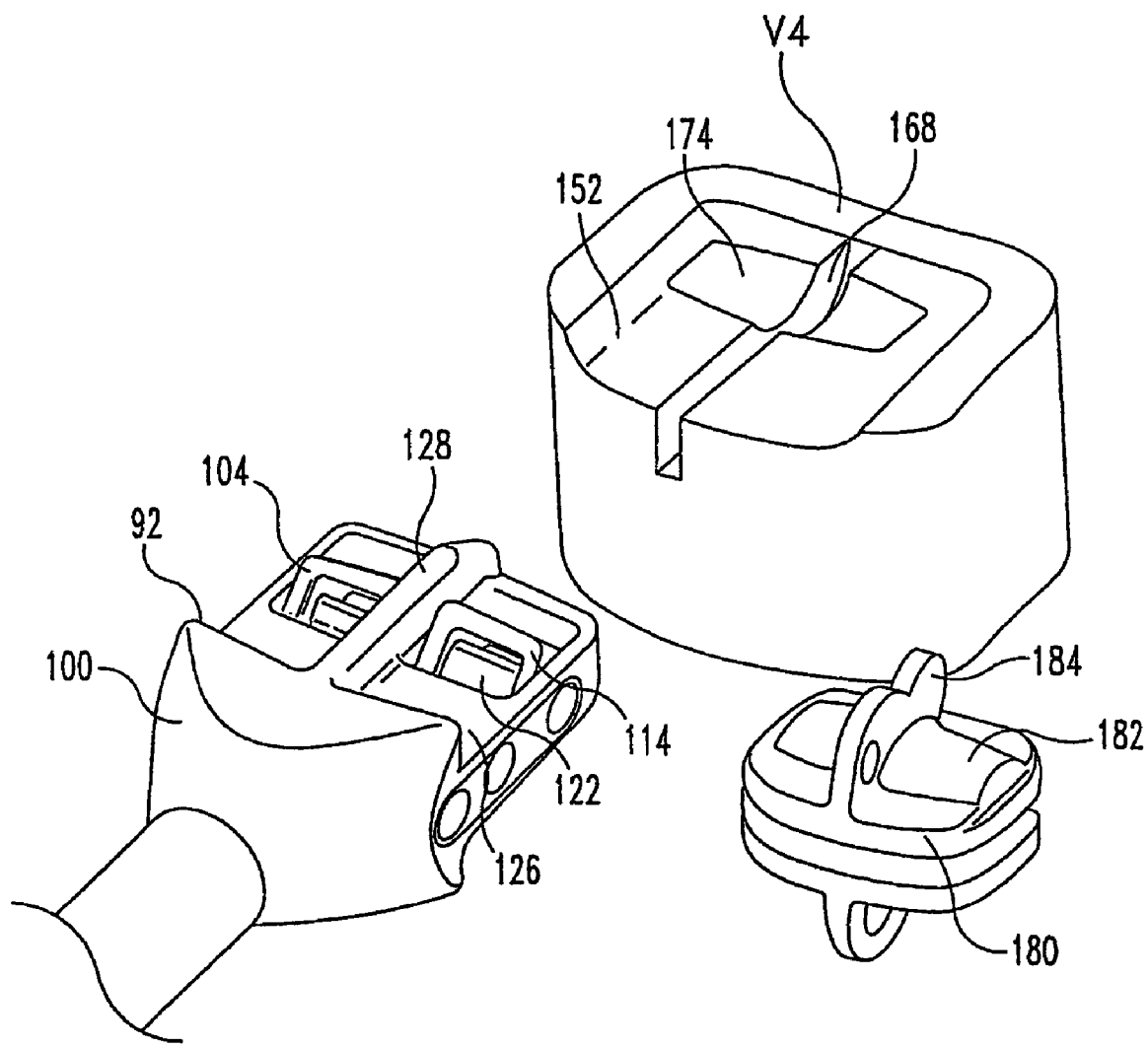
FIG. 9 illustrates one environment in which the FIG. 5 reamer is used.

As shown in FIG. 8 and in greater detail in FIG. 9, the guide member 128 of the central reamer 100 is slid into the center slot 168 formed in vertebra 14. Slot 168 along with the guide member 128 ensures that the reamer 100 is properly centered over vertebra V4. The stop surface 92 on the central reamer 100 ensures that the cutting members 104 are positioned at the right penetration depth over vertebra V4. To insert the central reamer into the disc space, the cutting members 104 of the reamer 100 are oriented such that the cutting blades 114 are flush with vertebrae engaging surfaces 126. Next, the reamer 100 is slid between the vertebrae V and positioned at the proper depth through stops 92, which engage a side of vertebra V4. Once fully inserted, the cutting members 104 can be rotated in order to form a kidney-shaped or curved surfaced cavity 174. After the kidney-shaped cavity 174 is reamed, a multi-axial spacer 180 can be inserted into cavity 174 and slot 168. To prevent expulsion of spacer 180, the spacer 180 includes opposing curved portions 182 that are conjugate with the formed kidney-shaped cavities 174 and fin portions 184 that are received within slot 168.

Figure 10:
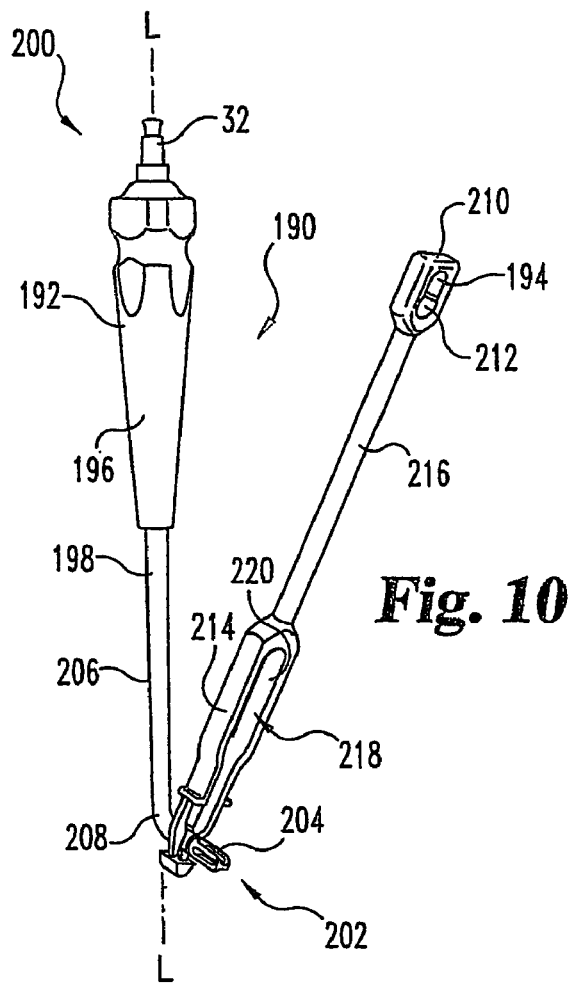
FIG. 10 illustrates an angled reamer assembly according to another embodiment.
Figure 11:
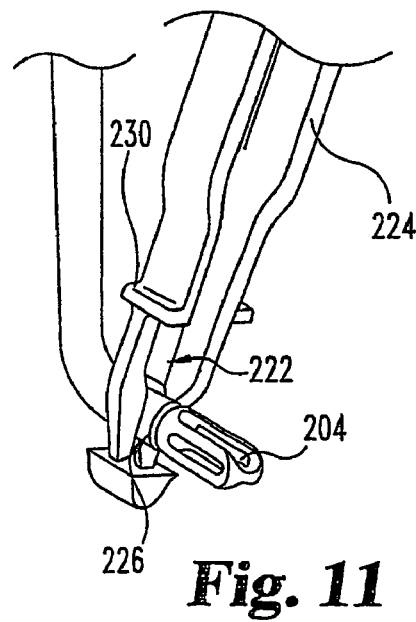
FIG. 11 illustrates an enlarged view of a head portion of the FIG. 10 reamer assembly.
Figure 12:
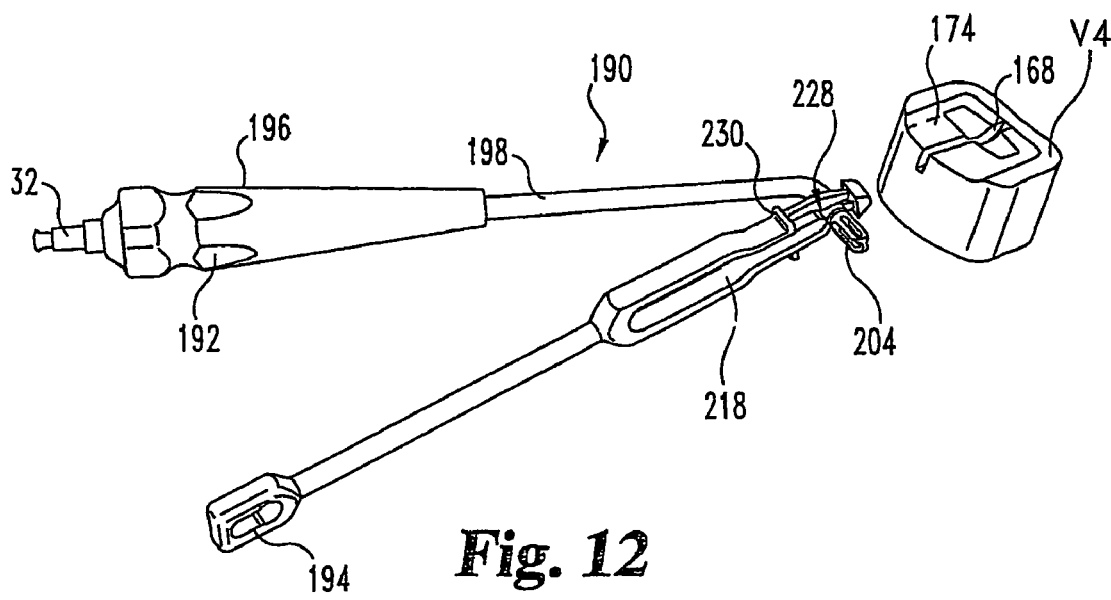
FIG. 12 illustrates a technique for disc space preparation with the FIG. 10 reamer assembly.

A curved reamer and guide assembly 190 for forming cavity 174 into vertebrae V according to another embodiment is illustrated in FIGS. 10-12. As illustrated, assembly 190 includes a curved reamer 192 slidably received within a reamer guide 194. The curved reamer 192 includes drive shaft 32 that is rotatably received within handled portion 96 196 and hollow curved shaft 198. The drive shaft 32 is configured to connect to rotary drive 24. The curved reamer 192 has a proximal end portion 200 at which the drive shaft 32 is received, and a distal end portion 202 at which a rotary cutting bit tool 204 is positioned. In the illustrated embodiment, the rotary cutting bit 204 is connected to the drive shaft 32 through a cable such that when the drive shaft 32 rotates, the rotary cutting bit 204 rotates. As illustrated, the curved shaft 198 includes a straight portion 206 and a bent or curved portion 208, which is angled in an oblique angle with respect to longitudinal axis L of the curved reamer 192.

The reamer guide 194 includes a handle end portion 210 with a cavity 212, a guide end portion 214 and a solid shaft 216 connecting the handle end portion 210 to the guide end portion 214. The guide end portion 214 of guide 194 defines a guide cavity 218 in which curved portion 208 of reamer 192 is received. The guide cavity 218 is further subdivided into a insertion portion 220 in which the reamer 192 is initially inserted outside the vertebrae V, and a reamer portion 222 at which the curved reamer 192 reams kidney-shaped cavity 194 in the vertebrae V. The insertion portion 220 includes a pair of oppositely disposed guide flanges 224, which prevent the reamer 192 from accidentally cutting into the vertebrae V at the wrong location. At the reamer portion 222 notches 226 are formed in flanges 222 to act as a template for the rotary cutting tool 204 such that tool 204 is able to move and cut cavity 174 into the vertebrae. Guide fins 228 extend from the reamer guides 194 in order to align the reamer guide 194 in the center slot 168. Stop members 230 are oriented perpendicular to the guide fins 228 to prevent the reamer guide 194 from being inserted too deeply into the disc space.

During use, the guide fins 228 are inserted into slots 168 formed in the vertebrae V. Once the stop members 230 prevent further insertion of the guide 194 into the disc space, the curved portion 208 of the reamer 192 is inserted into the insertion portion 220 of the guide cavity 218. Next, the curved portion 208 is slid through the guide cavity 218, past the guide flanges 224, and into notches 226 of the reamer portion 222 at which the rotary cutting member 204 can be moved in order to ream out kidney-shaped cavity 228. As previously mentioned, the guide flanges 224 as well as the notches 226 ensure that cavity 174 is formed at the proper location. Once cavity 174 is reamed, the reamer 192 along with the guide 194 can be removed from the disc space, and implant 180 can be implanted between the vertebrae V.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An oscillating rasp for preparation of vertebral endplates, comprising:
    a rotary power source;
    a linkage assembly coupled to said rotary power source to convert rotary motion of said rotary power source into reciprocating motion of a portion of the linkage assembly; and
    a pair of bilateral rasp plates positioned on opposite sides of a longitudinal axis, said rasp plates being linked to said linkage assembly and adapted to linearly reciprocate in opposite directions relative to each other along said longitudinal axis in response to the reciprocating motion provided by said linkage assembly, wherein each of said rasp plates includes a plurality of rows of cutting members and each of said plurality of rows includes a plurality of cutting members; and
    a head portion including a cavity within which said pair of bilateral rasp plates are housed, said head portion at least partially surrounding said pair of bilateral rasp plates to limit an amount of material removed from the vertebral endplates.

2. The rasp of claim 1, wherein said linkage assembly includes:
    a crankshaft coupled to said rotary power source and including a pair of cranks;
    a pair of connecting-rods coupled to said pair of cranks at opposite sides to convert the rotary motion of said rotary power source into the reciprocating motion; and
    a pair of members coupling said pair of bilateral rasp plates to said pair of connecting rods.

3. An oscillating rasp for preparation of vertebral endplates, comprising:
    a rotary power source;
    a linkage assembly coupled to said rotary power source to convert rotary motion of said rotary power source into reciprocating motion and
    a pair of bilateral rasp plates positioned on opposite sides of a longitudinal axis, said rasp plates being linked to said linkage assembly and adapted to linearly reciprocate in opposite directions relative to each other along said longitudinal axis in response to the reciprocating motion of said linkage assembly, wherein each of said rasp plates includes a plurality of rows of cutting members and each of said plurality of rows includes a plurality of cutting members; and
    wherein said pair of bilateral rasp plates have vertebrae cutting surfaces formed on opposite sides; and
    a head portion including a cavity within which said pair of bilateral rasp plates are housed, said head portion at least partially surrounding said pair of bilateral rasp plates to limit an amount of material removed from the vertebral endplates.

4. The rasp of claim 1, wherein said head portion further includes at least one stop member to limit penetration of said rasp plates into the vertebral endplates.

5. The rasp of claim 1, wherein one of said pair of bilateral rasp plates defines a groove and the other has a tongue member slidably received in said groove to align said pair of bilateral rasp plates with one another.

6. The rasp of claim 1, wherein said rotary power source includes a pneumatic motor.

7. An oscillating rasp for preparation of vertebral endplates, comprising:
    a rotary power source;
    a linkage assembly coupled to said rotary power source to convert rotary motion of said rotary power source into reciprocating motion;
    a pair of bilateral rasp plates positioned on opposite sides of a longitudinal axis, said rasp plates being linked to said linkage assembly and adapted to linearly reciprocate in opposite directions relative to each other along said longitudinal axis in response to the reciprocating motion of said linkage assembly; and
    a head portion within which said pair of bilateral rasp plates are housed, said head portion including a u-shaped member surrounding said pair of bilateral rasp plates to limit an amount of material removed from the vertebral endplates, said head portion further including at least one stop member to limit penetration of said rasp plates into the vertebral endplates;
    wherein said linkage assembly includes:
        a crankshaft coupled to said rotary power source and including a pair of cranks,
        a pair of connecting-rods coupled to said pair of cranks at opposite sides to convert the rotary motion of said rotary power source into the reciprocating motion, and
        a pair of members coupling said pair of bilateral rasp plates to said pair of connecting rods;
    wherein said pair of bilateral rasp plates have vertebrae cutting surfaces formed on opposite sides; and
    wherein one of said pair of bilateral rasp plates defines a groove and the other has a tongue member slidably received in said groove to align said pair of bilateral rasp plates with one another.

8. An oscillating rasp for preparation of vertebral endplates, comprising:
    a rotary power source;
    a linkage assembly coupled to said rotary power source to convert rotary motion of said rotary power source into reciprocating motion; and
    a head portion including an upper surface positioned opposite of a lower surface, and extending between a proximal end and a distal end positioned distally of a pair of bilateral rasp plates adapted to linearly reciprocate, said pair of bilateral rasp plates housed within a cavity in said head portion, said rasp plates each including an upper cutting surface extending through said upper surface and a lower cutting surface extending through said lower surface, said head portion at least partially surrounding said pair of bilateral rasp plates to limit an amount of material removed from the vertebral endplates.

9. The rasp of claim 8, wherein said bilateral rasp plates are linked to said linkage assembly and adapted to linearly reciprocate in opposite directions relative to each other in response to the reciprocating motion of said linkage assembly.

10. The rasp of claim 8, wherein said linkage assembly includes:
   a crankshaft coupled to said rotary power source and including a pair of cranks;
   a pair of connecting-rods coupled to said pair of cranks at opposite sides to convert the rotary motion of said rotary power source into the reciprocating motion; and
   a pair of members coupling said pair of bilateral rasp plates to said pair of connecting rods.

11. The rasp of claim 8, wherein one of said pair of bilateral rasp plates defines a groove and the other has a tongue member slidably received in said groove to align said pair of bilateral rasp plates with one another.

12. The rasp of claim 8, wherein said head portion includes a tapered insertion portion.

13. An oscillating rasp for preparation of vertebral endplates, comprising:
   a rotary power source;
   a linkage assembly coupled to said rotary power source to convert rotary motion of said rotary power source into reciprocating motion; and
   a head portion extending along a longitudinal axis between a proximal end and a distal end positioned distally of a pair of bilateral rasp plates adapted to linearly reciprocate along said longitudinal axis, said pair of bilateral rasp plates housed within a cavity in said head portion, said head portion including a pair of stop surfaces extending away from one another from a location on said head portion adjacent to said proximal end and transversely to said longitudinal axis, said head portion at least partially surrounding said pair of bilateral rasp plates to limit an amount of material removed from the vertebral endplates.

14. The rasp of claim 13, wherein said rasp plates each include a pair of oppositely positioned cutting surfaces extending through said opposite sides of said head portion.

15. The rasp of claim 13, wherein said bilateral rasp plates are linked to said linkage assembly and adapted to linearly reciprocate in opposite directions relative to each other in response to the reciprocating motion of said linkage assembly.

16. The rasp of claim 13, wherein said linkage assembly includes:
   a crankshaft coupled to said rotary power source and including a pair of cranks;
   a pair of connecting-rods coupled to said pair of cranks at opposite sides to convert the rotary motion of said rotary power source into the reciprocating motion; and
   a pair of members coupling said pair of bilateral rasp plates to said pair of connecting rods.

17. The rasp of claim 13, wherein one of said pair of bilateral rasp plates defines a groove and the other has a tongue member slidably received in said groove to align said pair of bilateral rasp plates with one another.

* * * * *